United States Patent [19]

Godai et al.

[11] 4,185,921
[45] Jan. 29, 1980

[54] SURFACE FLAW DETECTOR

[75] Inventors: Tomokazu Godai, Kamakura; Yasuhito Takeuchi; Kozo Nakai, both of Fujisawa; Kazuo Takeuchi, Kamakura; Yoshihisa Morioka, Kawasaki, all of Japan

[73] Assignee: Kobe Steel Limited, Kobe, Japan

[21] Appl. No.: 870,497

[22] Filed: Jan. 18, 1978

[30] Foreign Application Priority Data

Jan. 19, 1977 [JP] Japan .................................. 52-4022

[51] Int. Cl.² ............................................ G01N 21/32
[52] U.S. Cl. .................................... 356/426; 198/415; 209/701
[58] Field of Search ...................... 198/344, 379, 415; 356/200, 196, 209, 237, 238, 426, 430, 431, 445–448; 209/701

[56] References Cited

U.S. PATENT DOCUMENTS

| | | | |
|---|---|---|---|
| 2,857,800 | 10/1958 | Stevens | 356/196 |
| 3,584,963 | 12/1968 | Wisner | 356/237 |
| 3,797,943 | 3/1974 | Nagao et al. | 356/200 |
| 3,901,381 | 8/1975 | Quinn | 198/344 X |
| 3,992,111 | 11/1976 | Roulier et al. | 356/200 |

Primary Examiner—John K. Corbin
Assistant Examiner—Bruce Y. Arnold
Attorney, Agent, or Firm—Oblon, Fisher, Spivak, McClelland & Maier

[57] ABSTRACT

A surface flaw detector includes a light source capable of generating a laser beam, a material conveyance means provided for conveying a material to be examined in the direction transverse to the axis of the material and designed to let the material rotate on its axis at a fixed position or along the direction of conveyance, means for scanning the laser beam on the surface and in the axial direction of the material which is rotating on its own axis, optical means adapted to transmit the light reflected from the surface of the material to form a stationary optic image of the scanning means, light receiving means provided at the image forming position, and processing means adapted to discriminate the flaw signal upon receiving the output from the light receiving means.

3 Claims, 2 Drawing Figures

SURFACE FLAW DETECTOR

BACKGROUND OF THE INVENTION

1. Field of the Art

This invention relates to a surface flaw detector, and more particularly to a device for detecting any flaw existing in the surface of a substantially circular-sectioned rod- or bar-shaped material.

2. Description of the Prior Art

Welding rod is a typical example of a circular-sectioned material which is contemplated to be examined by the device of this invention. In manufacture of such welding rods, every produced rod is subjected to a visual test to check for any surface flaw at a stage immediately before the final packaging step so as to ensure the quality (commercial value) and specified performance of the welding rods in use.

The welding rods are likely to suffer flaws attributable to partial strip-off of the coating flux or development of cracks formed in the axial direction or ring cracks in the flux in their production process, particularly in the coating or drying step, so that it is essential to detect such flaws for ensuring the quality of the products.

Heretofore, the produced welding rods have been examined one by one visually by the inspector in the final step of the production process and sorted out according to the type and size of the flaw.

Such one-by-one rod surface visual inspection, however, is very time-consuming, and also fatigue of the inspector is multiplied as the inspection speed increases, resulting in a warped sense of judgment of the inspector or even misled inspection. Thus, there was a danger that the flawed welding rods be passed over and erroneously judged as conforming products.

Various kinds of surface flaw detectors utilizing the light beams have been proposed in U.S. Pat. No. 3,430,055 and many other patents, but none of these proposals provides a satisfactory solution to the above-said problems.

SUMMARY OF THE INVENTION

The first object of this invention is to provide a surface flaw detector capable of automatic surface inspection of the circular-sectioned rod or bar articles such as welding rods.

The second object of this invention is to provide a surface flaw detector of the said type, which is outstanding in its high accuracy of detection.

In order to implement the above-said and other objects of this invention, there is provided according to one aspect of this invention a surface flaw detector including a light source capable of generating a laser beam, a material conveyance means adapted for rotating the material being inspected on its own axis in the direction orthogonal to the axis of the material, means for scanning the laser beam on the surface and in the axial direction of the material which is rotating on its axis, optical means adapted to transmit the light reflected from the material surface to form a stationary optical image of the scanning means, light receiving means provided at the image forming position, and processing means adapted for discriminating the flaw signal upon receiving the output from the light receiving means.

According to another aspect of this invention, there is provided a surface flaw detector of the above-said type, wherein the material conveyance means includes a material acceleration conveyor assembly and a material carrying conveyor assembly, and the speed of rotation of the material on the carrying conveyor assembly can be controlled by the acceleration conveyor assembly.

It is also contemplated in this invention to provide a surface flaw detector of the above-described type, further characterized in that the sectional shape of the laser beam used is elongated in the direction orthogonal to the axis of the material when the beam is applied on the surface of the material.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views, and wherein.

DETAILED DESCRIPTION OF THE PREFERRED EMBODIMENT

Figure 2:
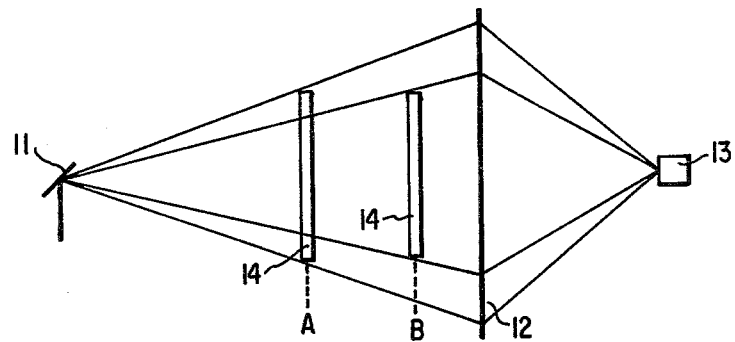
FIG. 2 is an arrangement plan of the principal parts of the embodiment of FIG. 1.

The device of this invention comprises a combination of an optical flaw detector unit and a material rotating and conveying system designed to allow surface inspection along the full length and full circumference of a rod- or bar-shaped material such as welding rod, said optical flaw detector unit comprising a scanning mirror 11 adapted to linearly scan the laser beam in a predetermined space, a condensing optical system 12 and a light receiver 13 which are arranged as shown in FIG. 2 relative to the welding rod 14 so that a stationary image of the optical point of the scanning mirror will be formed on the light receiving face of the light receiver by the light which has acted with the welding rod surface. The welding rod rotating and conveying system is composed of a welding rod feed mechanism, a welding rod rotating mechanism designed to rotate each welding rod at a fixed position or along the direction of movement, and a welding rod discharging mechanism. The welding rod feed mechanism functions to feed the welding rods to the rotating mechanism while keeping the welding rods aligned axially with the scanning direction of the scanning mirror, and the welding rod rotating mechanism is so constructed as to let each welding rod rotate on its axis at the scanning position of the scanning mirror so that the mirror will be able to scan over the full length and full circumference of the welding rod surface. The welding rod discharging mechanism is designed to remove the inspected rod out of the scanning position. Owing to a combination of an optical flaw detector capable of detecting surface flaw on the welding rod from a diffractive operation and a welding rod rotating and conveying system capable of continuous prosecution of the feeding, rotating and discharging steps while carrying the welding rod such that the optical flaw detector is positioned on the front or back side of the welding rod being examined relative to the direction of advancement, the device of this invention can release the inspector from the time-consuming inspection work to realize a significant saving of labor and rationalization of the inspection operation with a great economical effect. Use of a laser light source is advantageous as it allows enlargement of the ratio between the noise signal associated with the constitutional components of the welding rod and the flaw signal to make the device resistant to noise and free of erroneous detection or oversight, resulting in a phenomenal improvement of the inspection reliability.

The device of this invention will now be described in further detail by way of an embodiment thereof while having reference to the accompanying drawings.

Figure 1:
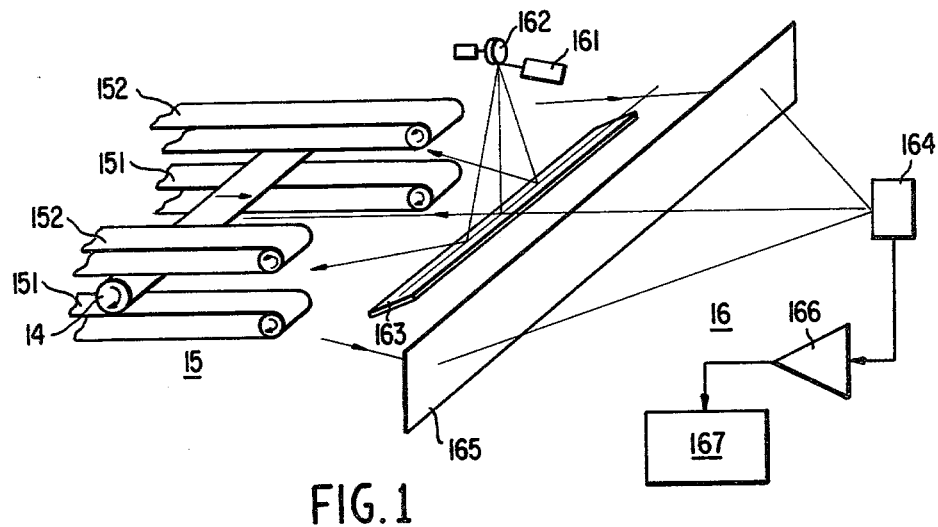
FIG. 1 is a diagrammatic illustration of one embodiment of this invention.

Referring to FIG. 1, the device of this invention includes essentially a welding rod rotating and conveying system 15 and an optical flaw detector unit 16, the rotating and conveying system 15 including a belt conveyor assembly 151 for carrying the welding rods 14 in the direction of the arrow and an acceleration conveyor assembly 152 arranged such that each welding rod 14 carried by the belt conveyor assembly 151 will make a rotating movement around its own axis on the upper side of the conveyor assembly, at least at the location close to the delivery end of the assembly. The welding rods 14 are placed at suitable intervals on the conveyance belt conveyor assembly 151 such that they are axially arranged transversely to the direction of movement of the belt conveyor assembly 151. Each welding rod 14 carried on the belt conveyor assembly 151 is forced to rotate on its own axis by the acceleration belt conveyor assembly 152 disposed close to the delivery end and transferred onto a discharging belt conveyor assembly (not shown) at the delivery end and thereby carried away to a place not causing any impediment to the inspection operation.

The optical flaw detector 16 includes a laser light source 161 which emanates a light beam, a scanning mirror 162 adapted to reflect the laser beam from the light source 161 and perform linear scanning at a predetermined space, a mirror 163 disposed at the predetermined space and on the feed side of the rotating and carrying system so that the rays of laser light coming from the scanning mirror 162 will be reflected on the mirror and directed toward the welding rod 14 carried and held between the conveyance belt conveyor assembly 151 and acceleration belt conveyor assembly 152 on the delivery side of the system 15 for scanning the surface of the welding rod axially thereof, a condensing device 165 whereby the light rays which have passed the mirror 163 are condensed to form a stationary image of the reflected light on the light receiving face of a light receiver 164, an amplifier 166 whereby the output signal from the light receiver 164 is converted into an input signal, and a processing unit whereby the output of the amplifier 166 is processed for crest discrimination or width discrimination by an operation such as differentiation to automatically judge whether there is any flaw or not. A stationary image of the optical point of the scanning mirror 162 corresponding to the surface condition of the scanning point on the welding rod surface is formed on the light receiving face of the light receiver 164, and the signal level corresponding to the light quantity is discriminated by a conventional processing device 167, thus accomplishing inspection along the full length and full circumference of the round surface of each welding rod.

In operation of the device of this invention having the above-described structural arrangements, each welding rod 14 to be examined is carried toward the optical flaw detector unit 16 while rotated around its own axis by the operation of the conveyance belt conveyor assembly 151 and acceleration belt conveyor assembly 152 of the welding rod rotating and conveying system 15 and is scanned by the laser beam at the front side in the direction of advancement of the welding rod 14 and in the axial direction thereof. As the scanning speed is far higher than the rotating speed of the welding rod, the entire surface of the welding rod is scanned while the welding rod makes one rotation. The information on the surface condition of the welding rod at the scanning point is provided as a change in the stationary image of the scanning point which is formed on the light receiving face of the light receiver, and such change is detected by the light receiver 164 and transferred into the processing device 167 which judges whether any flaw is present or not. A signal indicating the presence or absence of flaw is output from the output side of the processing device 167 for each welding rod.

As the feed, rotation and discharge of the welding rods are performed successively by the cooperation of the carrying belt conveyor assembly 151 and acceleration belt conveyor assembly 152, the flow of welding rods 14 on the conveyor system is accomplished smoothly and, further, the judgment of whether a flaw exists by the optical flaw detector 16 is sped up. Moreover, since the laser beam is applied to the surface of the welding rod on the front or back side in the direction of movement, there is no fear of committing erroneous detection even if the welding rod 14 is moved from the position of A to the position of B as shown in FIG. 2. Thus, the inspection operation is unaffected by any change in the horizontal direction of movement of the rod, that is, any change in speed of the belt conveyors. If the ratio of the noise signals from the constitutional components to the flaw signals from the flawed parts is measured by a regular reflection system and the device of this invention according to the type of flaw, there are provided the S/N ratios (S: flaw component signals, N: constitutional component noise signals) such as shown in the following table.

| Type of flaw | Regular reflection system - utilizing specular reflection from a coating surface. | Device of this invention |
| --- | --- | --- |
| Strip-off | 1 | 4–5 |
| Axial cracks | 1–3 | 8–9 |
| Ring cracks | 1 | 5–7 |
| Scratches | — | 4 |

As it is actually possible to detect the flaw if the value of S/N ratio is greater than 3, the device of this invention is very excellent in the ability of detecting various types of flaws and also high in accuracy of flaw detection.

While the present invention has been described by way of an embodiment where the welding rod rotating and conveying system is composed of the belt conveyor assemblies arranged to carry and rotate the respective welding rods to be examined, the principle of this invention is not limited to such arrangement; the welding rod feeding mechanism, the rotating mechanism for rotating each welding rod at a fixed position and the welding rod discharging mechanism may be arranged in a functionally separate relation to each other. This arrangement is suited for inspection at low speed. The sectional shape of the light beam used for scanning the welding rod surface needn't be circular. The beam may be so shaped as to be short in the scanning direction and elongated in the direction orthogonal to the scanning direction when applied on the material surface. In this case, the influence from vertical variation of the welding rod is minimized to allow a wider scope of tolerance for vertical variation of the welding rods during carriage thereof, thus providing a greater versatility to designing of the welding rod rotating and conveyance system.

As reviewed above, this invention provides a surface flaw detector which is capable of automatic flaw inspection along the entire length and entire circumference of the welding rod surface with sped-up inspecting performance and high accuracy of inspection.

Obviously numerous modifications and variations of the present invention are possible in light of the above teachings. It is therefore to be understood that within the scope of the appended claims, the invention may be practiced otherwise than as specifically described herein.

What is claimed as new and intended to be covered by Letters Patent is:

1. A surface flaw detector comprising a light source for generating a laser beam, a material conveyance means for conveying the material to be inspected in the direction transverse to the axis of said material while rotating said material around its axis, means for scanning said laser beam on the full length and circumference of the surface and in the axial and conveying direction of the material while said material is rotating on its axis and being conveyed, optical means for forming a stationary optical image of said scanning means with the light reflected from the material surface, light receiving means provided at the image forming position, and processing means which receives the output from said light receiving means to discriminate the flaw signals.

2. The device according to claim 1, wherein said material conveyance means comprises a material acceleration conveyor assembly and a material carrying conveyor assembly, and the rotating speed of the material on said carrying conveyor assembly is controlled by said acceleration conveyor assembly.

3. The device according to claim 1, wherein the laser beam is so shaped in section that it is elongated in the direction orthogonal to the axis of the material when applied on the surface of the material.

* * * * *